US010028654B2

United States Patent
Bor et al.

(10) Patent No.: US 10,028,654 B2
(45) Date of Patent: Jul. 24, 2018

(54) SYSTEM AND METHOD FOR EYE ORIENTATION

(71) Applicant: AMO Development, LLC, Santa Ana, CA (US)

(72) Inventors: Zsolt Bor, San Clemente, CA (US); Anthony Dennison, Irvine, CA (US); Michael Campos, Fremont, CA (US); Peter Patrick De Guzman, Orange, CA (US)

(73) Assignee: AMO Development, LLC, Santa Ana, CA (US)

( * ) Notice: Subject to any disclaimer, the term of this patent is extended or adjusted under 35 U.S.C. 154(b) by 106 days.

(21) Appl. No.: 14/196,912

(22) Filed: Mar. 4, 2014

(65) Prior Publication Data

US 2014/0268042 A1 Sep. 18, 2014

Related U.S. Application Data

(60) Provisional application No. 61/800,164, filed on Mar. 15, 2013.

(51) Int. Cl.
*A61B 3/10* (2006.01)
*A61B 3/14* (2006.01)

(52) U.S. Cl.
CPC .............. *A61B 3/1005* (2013.01); *A61B 3/14* (2013.01)

(58) Field of Classification Search
CPC ...... A61F 2009/0087; A61F 2009/0088; A61F 2009/00882; A61B 3/0008; A61B 3/10;
(Continued)

(56) References Cited

U.S. PATENT DOCUMENTS 4,665,913 A 5/1987 L'Esperance, Jr.
4,669,466 A 6/1987 L'Esperance
(Continued)

FOREIGN PATENT DOCUMENTS

WO WO 2008003807 A1 * 1/2008 ............. A61B 3/113

OTHER PUBLICATIONS

A. Jóźwik ; D. Siedlecki ; M. Zając; Evaluation of intraocular lens implant location in the eyeball basing on the Purkinje images. Proc. SPIE 8697, 18th Czech-Polish-Slovak Optical Conference on Wave and Quantum Aspects of Contemporary Optics, 86970O, Dec. 18, 2012, pp. 1-6.*
(Continued)

*Primary Examiner* — Ricky Mack
*Assistant Examiner* — Gary O'Neill
(74) *Attorney, Agent, or Firm* — Johnson & Johnson Surgical Vision, Inc.

(57) ABSTRACT

Systems and methods for locating the center of a lens in the eye are provided. These systems and methods can be used to improve the effectiveness of a wide variety of different ophthalmic procedures. In one embodiment, a system and method is provided for determining the center of eye lens by illuminating the eye with a set of light sources, and measuring the resulting first image of the light sources reflected from an anterior surface of the lens and the resulting second image of the light sources reflected from a posterior surface of the lens. The location of the center of the lens of the eye is then determined using the measurements. In one embodiment, the center of the lens is determined by interpolating between the measures of the images. Such a determination provides an accurate location of the geometric center of the lens.

12 Claims, 9 Drawing Sheets

(58) Field of Classification Search
CPC ..... A61B 3/107; A61B 3/1005; A61B 3/1015; A61B 3/113; A61B 3/1173; A61B 3/1176; A61B 3/14
USPC .......................... 351/205–208, 214, 221, 246
See application file for complete search history.

(56) References Cited

U.S. PATENT DOCUMENTS

| | | | | |
|---|---|---|---|---|
| 4,732,148 | A | 3/1988 | L'Esperance, Jr. | |
| 4,764,930 | A | 8/1988 | Bille et al. | |
| 4,770,172 | A | 9/1988 | L'Esperance, Jr. | |
| 4,773,414 | A | 9/1988 | L'Esperance, Jr. | |
| 5,108,388 | A | 4/1992 | Trokel et al. | |
| 5,163,934 | A | 11/1992 | Munnerlyn | |
| 5,207,668 | A | 5/1993 | L'Esperance, Jr. | |
| 5,219,343 | A | 5/1993 | L'Esperance, Jr. | |
| 5,646,791 | A | 7/1997 | Glockler | |
| 5,993,438 | A | 11/1999 | Juhasz et al. | |
| D462,442 | S | 9/2002 | Webb | |
| 6,623,476 | B2 | 9/2003 | Juhasz et al. | |
| 6,863,667 | B2 | 3/2005 | Webb et al. | |
| 7,338,169 | B2 | 3/2008 | Somani | |
| 7,611,507 | B2 | 11/2009 | Raksi et al. | |
| 7,931,371 | B2 | 4/2011 | Dai | |
| 7,931,374 | B2 | 4/2011 | Dai et al. | |
| 7,972,325 | B2 | 7/2011 | Stark et al. | |
| 7,976,163 | B2 | 7/2011 | Campbell et al. | |
| 7,988,292 | B2 | 8/2011 | Neal et al. | |
| 8,126,246 | B2 | 2/2012 | Farrer et al. | |
| 2002/0048456 | A1* | 4/2002 | Ohtani | G03B 17/00 396/51 |
| 2010/0134760 | A1* | 6/2010 | Salvati | A61B 3/0025 351/206 |
| 2011/0187995 | A1* | 8/2011 | Frey | A61F 9/00825 351/208 |

OTHER PUBLICATIONS

A. Jozwik ; D. Siedlecki; M. Zajqc; Evaluation of intraocular lens implant location in the eyeball basing on the Purkinje images . Proc. SPIE 8697, 18th Czech-Polish-Slovak Optical Conference on Wave and Quantum Aspects of Contemporary Optics, 869700, Dec. 18, 2012, pp. 1-6.*

Co-pending U.S. Appl. No. 13/230,590, filed Sep. 12, 2011.

* cited by examiner

300

SYSTEM AND METHOD FOR EYE ORIENTATION

CROSS-REFERENCES TO RELATED APPLICATIONS

This application claims priority to U.S. provisional application No. 61/800,164 filed on Mar. 15, 2013, the entire contents of which are incorporated herein by reference.

TECHNICAL FIELD

Embodiments of the present invention generally relate to vision techniques, and particularly to techniques for locating the center of different surfaces in the eye.

BACKGROUND

Many modern ophthalmic surgical procedures require an accurate determination of the location of the center of different surfaces in the eye. For example, during certain cataract surgical procedures, such as capsulorhexis, it is necessary to locate the center of the natural eye lens to remove the lens capsule. In cataract surgery, the natural lens is removed and replaced with an artificial intraocular lens (IOL). Due to mechanical and symmetry reasons, the implanted IOL moves to the center of the capsular bag, but the capsular bag is not visible to the surgeon during cataract surgery. Accurate determination of the natural lens location is generally required to allow the surgeon to most efficiently remove the natural lens and properly locate the implanted IOL. This is merely one example of the various ophthalmic procedures which require accurate determination of the center of a particular surface in an eye.

Unfortunately, however, conventional techniques for locating the center of the various surfaces in the eye have limited effectiveness and/or accuracy. For example, some techniques to determine the center of an eye lens use the center of the pupil as an approximation of the eye lens center. But, these techniques have limited accuracy as the geometric center of the lens does not always coincide with center of the dilated pupil.

Therefore, improved techniques for determining the location of the center of different surfaces in the eye are needed.

BRIEF SUMMARY OF THE INVENTION

Embodiments of this invention generally provide improved systems and methods for locating the center of different surfaces in the eye, including for example, the center of an eye lens. These systems and methods can be used to improve the effectiveness of a wide variety of different ophthalmic procedures requiring accurate determination of the lens center. One embodiment provides a system and method for determining the center of the lens by illuminating the eye with a set of light sources and utilizing the Purkinje reflections from the different surfaces of the eye to locate the center of the lens. In this measurement, the center locations of the Purkinje III reflection (anterior surface of the lens) and Purkinje IV reflection (posterior surface of the lens) are determined. The location of the center of the lens of the eye is then determined as the distance between the Purkinje III centroid and the Purkinje IV centroid. Such a determination provides an accurate location of the geometric center of the lens, and can be used for any procedure that requires a determination of the center of a surface within the eye. The geometric center of lens can then be determined for any procedure that requires locating an accurate center of the lens.

Reflected images can be generated using an arrangement of light sources that are configured to project a pattern of light onto the eye. For example, the light sources may be arranged in a semicircle and adapted to cause a first image of the semicircle to be reflected from an anterior surface of the lens in the eye, and a second image of the semicircle to be reflected from a posterior surface of lens. Multiple illumination sources can be utilized for such measurements as well, as long as the detector used to capture the reflections has enough light to be able to record the images. This source can vary from visible to infrared (IR), as long as the detector is calibrated for the wavelength being utilized. It should be noted that such a determination of the lens center can be made without performing an invasive procedure in the eye or in the lens capsule during a surgical procedure. Rather, the determination can be made in the pre-operative or post operative phases, allowing a robust measurement for any given circumstance in which the center location of the lens needs to be determined.

Other methods can be used with this method to determine the center of the lens by Purkinje reflections. One of the most important measurements in LASIK (Laser Assisted In Situ Keratomileusis) surgery and cataract surgery is the wavefront measurement. Aberration measurements of the whole eye are taken to determine how the wavefront of light propagates through the eye onto the retina. The more aberrations that are present, the lower the resolution and the quality of vision. Typically, multiple measurements are made on the eye to determine the quality of the structures besides wavefront. For example, a slit lamp is used to determine cornea thickness and quality. However, a new method described here can be used as a modification to the slit lamp approach to enhance the ability to visualize a capsular bag holding the lens. Since the iris is technically 'invisible' under infrared illumination, a slit lamp can be modified with an IR illumination source to allow one to visualize the whole capsular bag. This would enable one to determine the location of the lens in eye as well as the eye, and could be used in combination with the Purkinje reflections to determine the center of the lens. As such, when the patient is transferred from the diagnostic machine to the surgical room, the differences in Purkinje measurements can be compared and used as reference to ascertain precisely the size and the location of the capsular bag during surgery.

This summary and the following detailed description are merely exemplary, illustrative, and explanatory, and are not intended to limit, but to provide further explanation of the invention as claimed. Additional features and advantages of the invention will be set forth in the descriptions that follow, and in part will be apparent from the description, or may be learned by practice of the invention. The objectives and other advantages of the invention will be realized and attained by the structure particularly pointed out in the written description, claims and the appended drawings.

BRIEF DESCRIPTION OF THE DRAWINGS

Understanding this invention will be facilitated by the following detailed description of the preferred embodiments considered in conjunction with the accompanying drawings, in which like numerals refer to like parts. Note, however, that the drawings are not drawn to scale.

DETAILED DESCRIPTION OF THE INVENTION

The drawings and related descriptions of the embodiments have been simplified to illustrate elements that are relevant for a clear understanding of these embodiments, while eliminating various other elements found in conventional collagen shields, ophthalmic patient interfaces, and in laser eye surgical systems. Those of ordinary skill in the art may thus recognize that other elements and/or steps are desirable and/or required in implementing the embodiments that are claimed and described. But, because those other elements and steps are well known in the art, and because they do not necessarily facilitate a better understanding of the embodiments, they are not discussed. This disclosure is directed to all applicable variations, modifications, changes, and implementations known to those skilled in the art. As such, the following detailed descriptions are merely illustrative and exemplary in nature and are not intended to limit the embodiments of the subject matter or the uses of such embodiments. As used in this application, the terms “exemplary” and “illustrative” mean “serving as an example, instance, or illustration.” Any implementation described as exemplary or illustrative is not meant to be construed as preferred or advantageous over other implementations. Further, there is no intention to be bound by any expressed or implied theory presented in the preceding background of the invention, brief summary, or the following detailed description.

Figure 1:
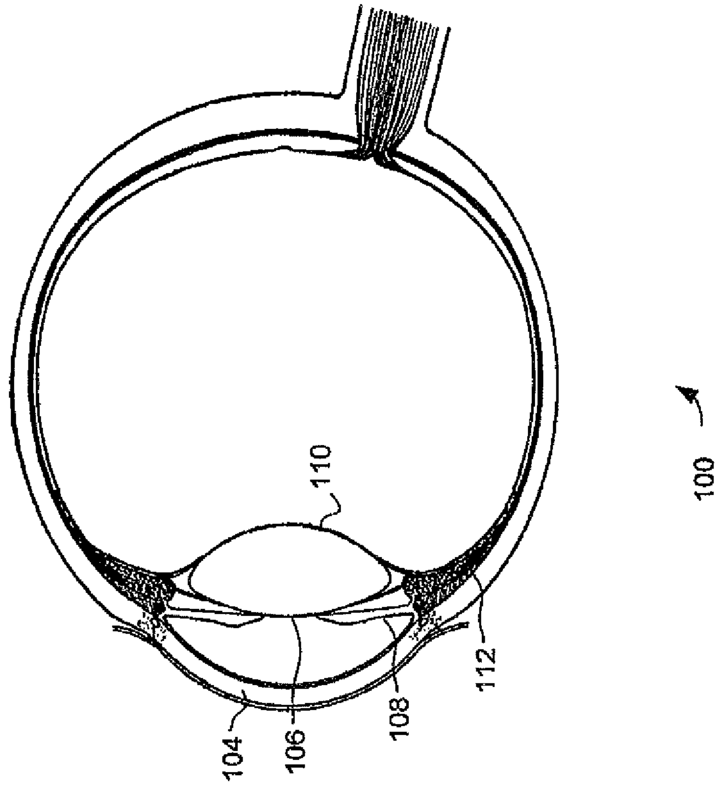
FIG. 1 is a cross-sectional side view of a human eye.

Turning to the drawings, FIG. 1 illustrates a simplified cross-sectional view of an exemplary human eye 100. In general, the eye 100 includes a cornea 104, a pupil 106, an iris 108, a lens 110, and ciliary muscle 114. The eye lens 110 has 4 main parts, namely: a lens capsule, a lens epithelium, the cortex and the nucleus. The lens capsule is a transparent membrane composed of collagen that completely surrounds the lens. The ciliary fibers connect directly to the capsule and through tension and relaxing cause the lens to increase or decrease in size, or to “accommodate” to focus in on objects. The lens epithelium is located at the anterior portion of the lens, between the lens capsule and the lens cortex. The lens never loses any cells throughout a person’s life, but rather gets more and more compact inside of the capsule bag. Thus, the oldest and most compact area is called the nucleus. Many of the hardest cataracts are formed here. The cortex is compromised of younger fibers that are between the nucleus and epithelium both on the anterior and posterior side of the lens. Though most of the focusing ability of the eye is done at the cornea, the lens also aids in precisely focusing light onto the retina. As such, the posterior side of the lens has a steeper radius of curvature than the anterior side to aid in this process. This will effect the Purkinje reflections seen from the posterior side and cause them to look larger.

As described earlier, many modern ophthalmic procedures require accurate determination of the location of the lens in the eye. In cataract surgery, the natural lens is removed and replaced with an artificial intraocular lens (IOL). Since the lens is surrounded completely by the capsule bag, a hole must be made in the bag in order to remove the lens. This procedure is known as a capsulorhexis which consists of creating a circle on the anterior side of the capsule bag. This hole can be created with multiple techniques. Most commonly used techniques use manual surgical tools like microkeratomes and forceps or an ultra-short pulsed laser that emits radiation with ultra-short pulse durations as long as a few nanoseconds, or as short as a few femtoseconds. The biggest difficulty with this procedure involves creating a circular opening in the center of the lens to ensure that the implanted artificial lens (Intraocular Lens or ‘IOL’) will sit level, center, and stable in the capsular bag once the lens is removed. Misalignment can lead to post-operative complications that typically require further surgery to adjust. Of course, this is just one of many different procedures for which an accurate determination of lens location is desirable. Embodiments of this invention generally provide improved systems and methods for locating the center of the lens in the eye preoperatively (diagnostic), during surgery, as well as post-operatively.

One embodiment provides a technique for determining the center of eye lens by illuminating the eye with a set of light sources and measuring the resulting first image of the light sources reflected from an anterior surface of the lens (Purkinje III) and the resulting second image of the light sources reflected from a posterior surface of the lens (Purkinje IV). In this measurement, the Purkinje III and Purkinje IV diameter and center location are determined. The location of the center of the lens of the eye is then determined using the distance between the Purkinje III center location and the Purkinje IV center location In this embodiment, a given situation can be utilized during a pre-operative diagnostic measurement to create a reference point for the center of lens for use during surgery.

Figure 2:
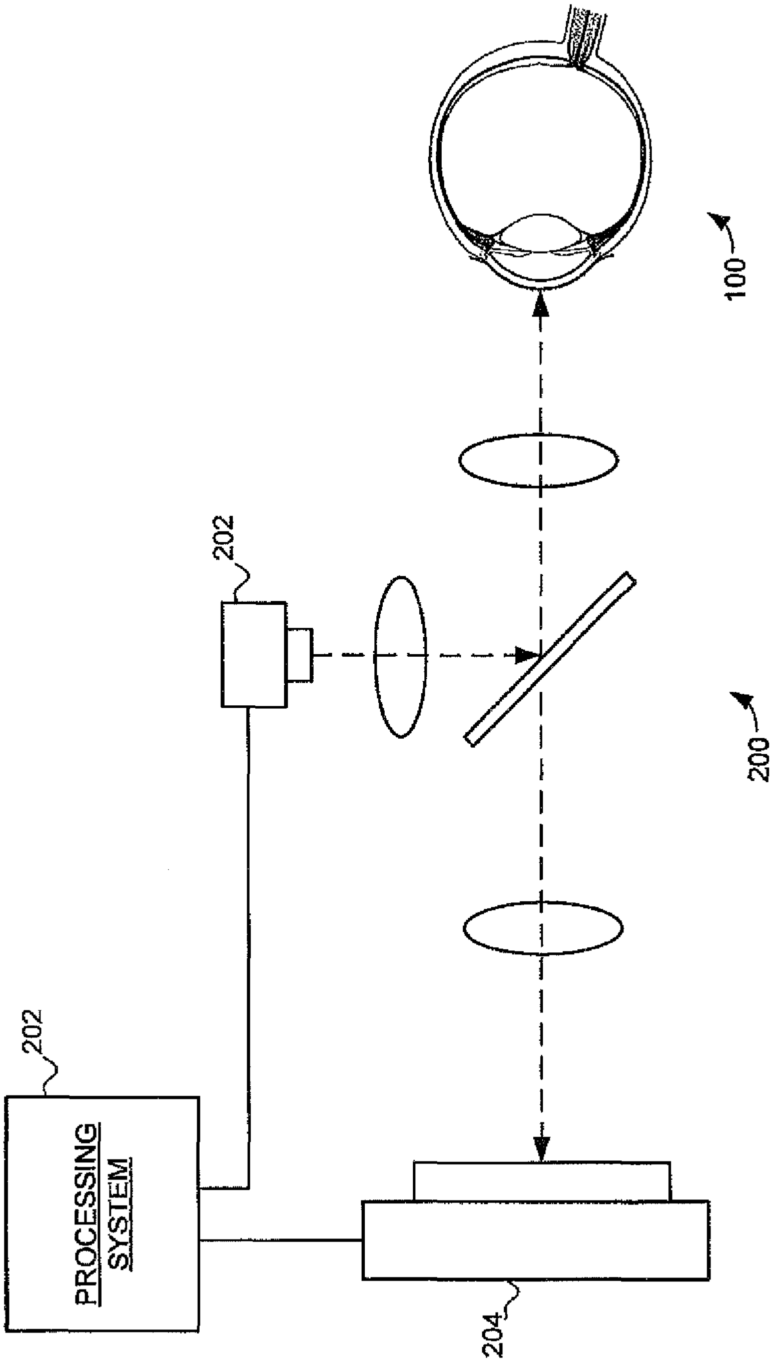
FIG. 2 is a schematic diagram of an eye lens location system according to an embodiment of the invention.

Turning now to FIG. 2, a simplified schematic view of a lens location determination system 200 is illustrated. The system 200 includes a light generator 202, a detector 204, and a processing system 206. In general, the light generator 202 and associated optical elements are configured to illuminate the eye 100 with a set of light sources. For example, the light generator 202 can comprise a set of light emitting diodes (LEDs) arranged in a semicircle and configured to illuminate the eye 100. Other suitable light sources can be used as well as multiple wavelengths. The detector can comprise a digital imaging device such as a charge coupled detector (CCD), CMOS Sensor or a photodiode. The detector 204 is configured to detect the resulting reflections from the eye 100. The detector is then connected to the processing system via USB, GigE (Ethernet), camera link, or another suitable method to transmit the raw analog signal to a data acquisition system. From there, the analog signal is converted to a digital signal to allow for the computer to utilize machine vision to locate the reflected light. Machine vision can then utilize the algorithm to determine the centroids of each Purkinje reflection and subsequently locate the center of the lens. Since this measurement will be done in real time, the camera should have a frame rate of greater than 30 Hz to enable the capture of most bulk movements of the eye. Faster frame rates will enable more fine motions to be captured and compensated for. Since the camera will be collecting frames at a given rate, the machine vision and DAQ (data acquisition) board should be able to import the data at least the same rate the camera captures the frames. As such, the machine vision should be configured to enable the tracking of the Purkinje images over a given field of view, essentially tracking the reflections as the moves. Given a reference point, this method could be a rough estimation for 2 axis (X and Y) eye tracking.

In any of these embodiments, the processing system 206 is configured to determine diameter and center location of both Purkinje III and Purkinje IV reflections. The processing system 206 can then determine the geometrical center of the lens of the eye using the distance between the Purkinje III center location and the Purkinje IV center location. It should be noted that such determinations can be used for either a natural lens in the eye, or for an implanted IOL. Hence, the processing system can determine the center of either a natural lens or an IOL. Furthermore, the system can be used for determinations even when the eye is applanated by a lens in a patient interface device during laser cataract surgery and LASIK procedures. Patient interfaces and applanating lenses used therein are described in greater detail below.

In one embodiment, the processing system 206 determines the location of the center of the lens by interpolating along a line between the centers of the Purkinje images. Specifically, the processing system 206 determines the center location of the eye lens by using the diameters of the Purkinje images and the distance between the centers of the Purkinje images to weigh the interpolation along the line. Using these Purkinje images and interpolation allows accurate determination of the geometric center of the lens, and can be used for any ophthalmic procedure requiring such determinations. These determinations can be made using the system 100 without performing any invasive acts in the eye or the lens capsule.

Figure 3:
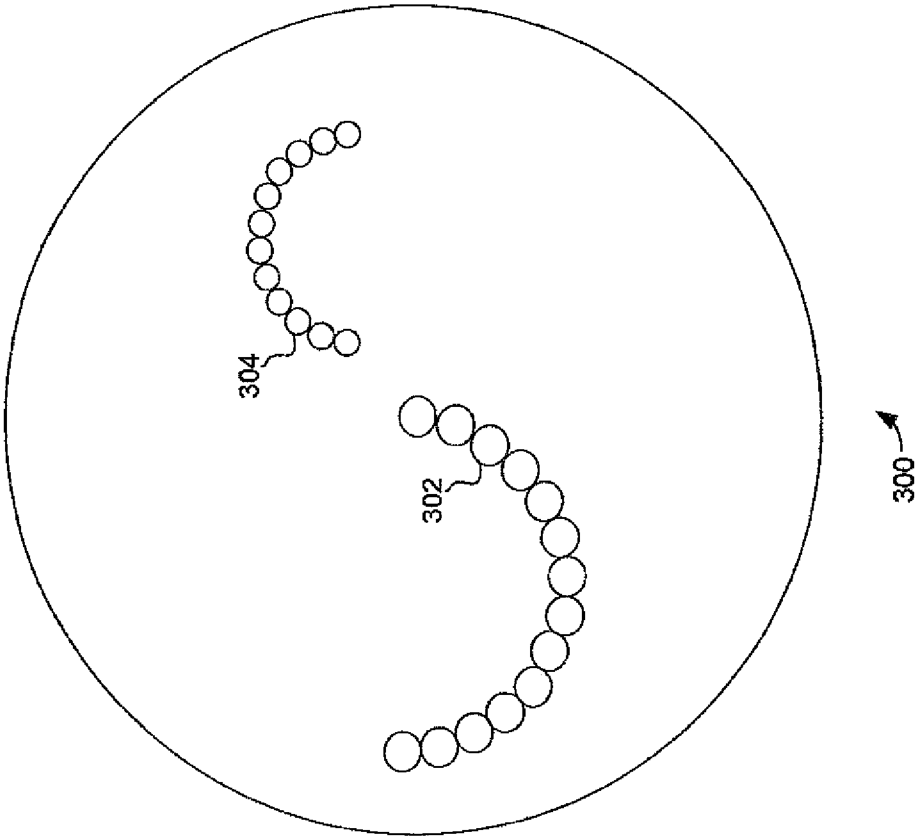
FIGS. 3-5 are front portion views of an eye with images formed according to an embodiment of the invention.

Turning now to FIG. 3, a front portion view of an eye 300 is illustrated. According to the techniques described in this application, the view of eye 300 also illustrates a first image 302 of light sources reflected from an anterior surface of lens (not shown in FIG.) and a second image 304 of light sources reflected from a posterior surface of lens. In this specific embodiment, the first image 302 reflected from an anterior surface of the lens comprises a portion of a Purkinje III circle, and the second image 304 reflected from a posterior surface of the lens comprises a portion of a Purkinje IV circle. Both the Purkinje III circle and Purkinje IV circle are illustrated as a collection of smaller circles, wherein each smaller circle represents the effect of one light source in the light generator. As has been described earlier, the Purkinje IV image will have a magnification associated to it due to the difference in radius of curvature of the posterior bag, causing the image to be inherently larger than the Purkinje III image. These include projection from a semicircle arrangement of light sources into the eye 300. Likewise, these images can be detected and measured using various types and configurations of sensors, previously described.

Figure 4:
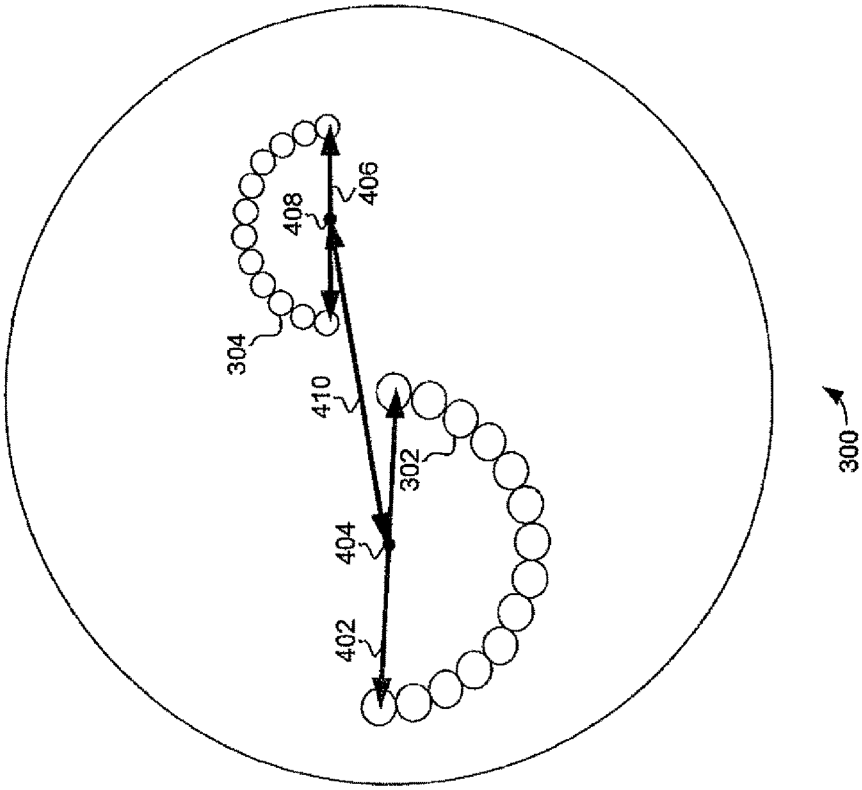

FIG. 4 illustrates a schematic view of the eye 300 showing measurements of the associated first image 302 and the second image 304. In this embodiment, a first diameter 402 and a first center location 404 of the first image are determined. In FIG. 4 the first diameter 402 is illustrated as the line extending across the first image 302, with the center location 404 as a point along the line. Likewise, a second diameter 406 and a second center location 408 of the second image are also determined. Again, the second diameter 406 is illustrated as the line extending across the second image 304, with the center location 408 as a point along the line. Finally, the distance 410 between the center locations is determined and is illustrated as the line between the center locations.

Figure 5:
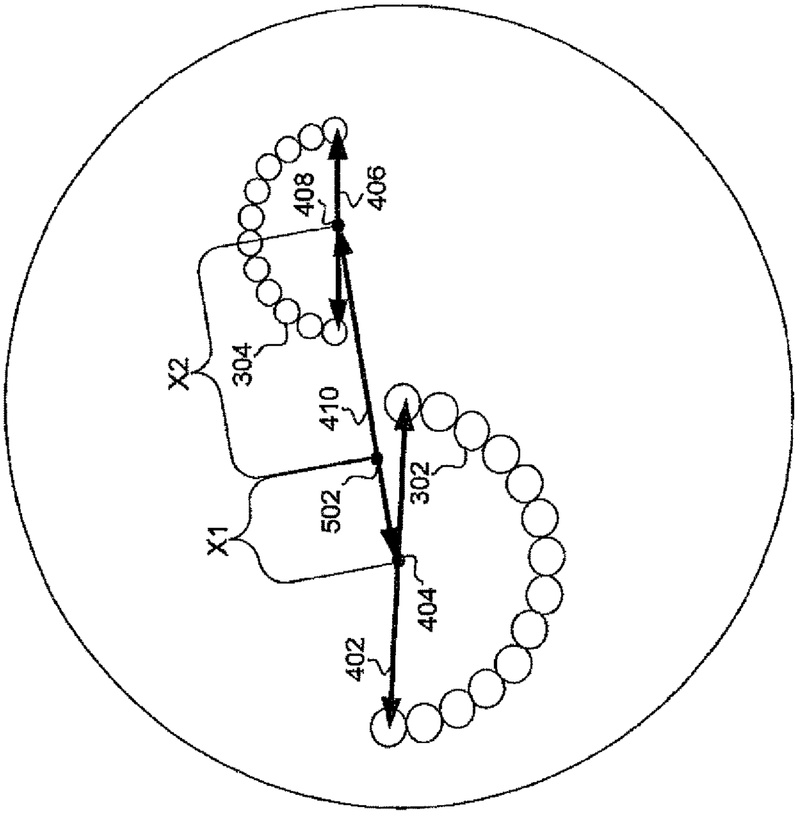

As described above, in one embodiment, the center of the lens is determined by interpolating between the first center location 404 and the second center location 408 based on the first diameter, the second diameter, and the distance between the first center location 406 and the second center location 408. The result of an exemplary interpolation is illustrated in FIG. 5. As shown in FIG. 5, the center of lens 502 is determined to be a distance $X_1$ from the first center location 404 and a distance $X_2$ from the second center location 408. It should be noted that this illustrated example is not necessarily drawn to scale. Furthermore, it should be noted that it may not be necessary to determine both $X_1$ and $X_2$ to determine the center of lens 502. Rather, in some embodiments, determining either the distance $X_1$ from the first center location 404 or the distance $X_2$ from the second center location 408 may be sufficient for purposes of determining the center of the lens 502.

As one specific example, the location of the center of the lens 502 can be determined as corresponding to a position on a line between the first center location and the second center location at a distance $X_1$ from the first center location 404, where $X_1$ is defined as:

$$X_1 = L\left(\frac{D_4}{D_3 + D_4}\right),$$

wherein L is defined as the distance between the first center location and the second center location, $D_3$ is defined as the first diameter, and $D_4$ is defined as the second diameter. In this case, the first diameter $D_3$ is the diameter of the Purkinje III circle, and the second diameter $D_4$ is the diameter of the Purkinje IV circle.

Figure 6:
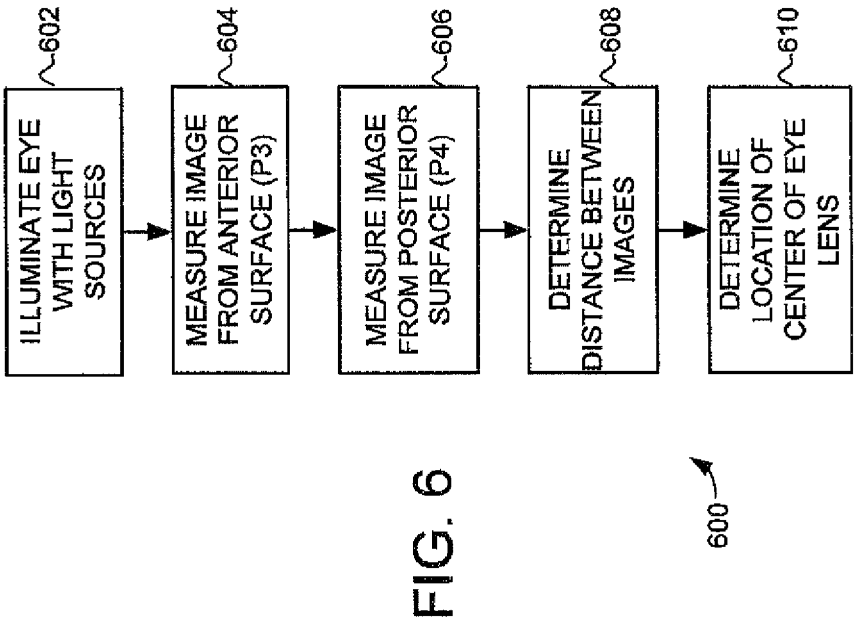
FIG. 6 is a flow diagram illustrating a method of determining a location of a lens in an eye according to an embodiment of the invention.

The location of the center of the lens 502 can also be determined as corresponding to a position on a line between the first center location and the second center location at a distance $X_2$ from the second center location, where $X_2$ is defined as:

$$X_2 = L\left(\frac{D_3}{D_3 + D_4}\right),$$

wherein L is defined as the distance between the first center location and the second center location, $D_3$ is defined as the first diameter, and $D_4$ is defined as the second diameter. This determination of $X_2$ can be an alternative to the determination of $X_1$ described above, or vice versa. Alternatively, the determinations of $X_1$ and $X_2$ described above can be combined within the software code to streamline the calculation to allow for minimal processing time, and therefore more real-time calculations and tracking FIG. 6 illustrates a method 600 for determining the location of a center of an eye. The first step 602 illuminates the eye with a set of light sources. As described above, in one embodiment, this step may be implemented using a set of light emitting diodes (LEDs) arranged in a semicircle and configured to illuminate the eye. Of course, other arrangements and shapes could be used. The second step 604 measures the resulting first image of the light sources reflected from an anterior surface of the lens. The next step 606 measures the resulting second image of the light sources reflected from a posterior surface of the lens. As one example of steps 604 and 606, in measuring the first image, a first diameter and a first center location of the first image can be determined, and in measuring the second image, a second diameter and a second center location of the second image can be determined. Such measurements can be implemented using any suitable image detection and processing mechanism. Furthermore, the steps 604 and 606 can comprise the capturing and measuring of a Purkinje III circle and a Purkinje IV circle, and the determining of a diameter and center location of each respective Purkinje circle. In other embodiments, other measurements, such as the size and location of the images can be used. For example, average or weighted widths/lengths and/or centroids of the images can be determined and used.

The next step 608 determines the distance between the images. Again, the distance between the images can be calculated using a variety of techniques. For example, the distance can be determined by calculating the distance between the center locations of the images. In another example, the distance can be determined by calculating the distance between centroids of the images.

The next step 610 determines the location of the center of the lens in the eye. For example, the location can be determined using the diameter of the images and the distance between the center locations. Or, in another example, the location can be determined using average or weighted widths and other measures of distance between images. In any such case, the center of the lens may be determined by interpolating between locations of the images based on the relative size and the position of the images. In one specific embodiment, the center of the lens is determined by interpolating between the first center location and the second center location based on the first diameter, the second diameter, and the distance between the first center location and the second center location.

Figure 7:
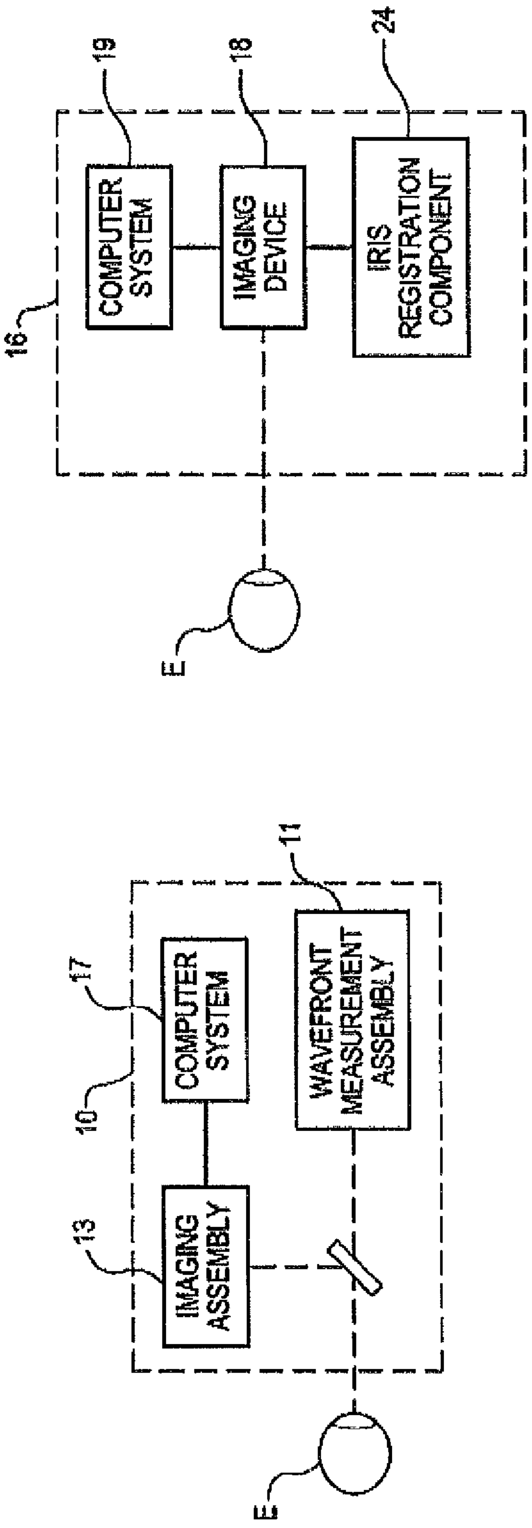
FIG. 7 is a diagram illustrating a first and second measurement system according to an embodiment of this invention.

The system 100 can be implemented as a stand-alone device or as part of either a larger diagnostic system or an ophthalmic laser system. For example, the system 100 can be implemented as part of a ophthalmic diagnostic and/or measurement system designed provide one or more of wavefront aberrometry, topography, autorefractometry, pupillometry, and optical coherence tomography. FIG. 7 illustrates a first measurement system 10 and a second measurement system 16. In an embodiment, the first measurement system 10 is a wavefront measurement device 10 that measures aberrations and other optical characteristics of an ocular or other optical tissue system. The data from such a wavefront measurement device may be analyzed by a computer system 17 and used to generate an optical surface from an array of optical gradients. The wavefront system combined with the system 100 can be used to quantify aberrations throughout the entire optical system of the patient's eye, including second-order aberrations related to spherical error and cylindrical errors and higher order aberrations related to coma, trefoil, and spherical aberrations. The system 100 may also be incorporated into and implemented as part of the Abbott iDesign™ Advanced WaveScan Studio aberrometer, which is a next-generation diagnostic tool that uses wavefront technology to map and analyze imperfections and abnormalities of the cornea, and to develop a suitable treatment plan prior to certain ophthalmic procedures, such as LASIK. Exemplary wavefront diagnostic systems are described in commonly-owned U.S. Pat. Nos. 7,931,371, 7,931,374, 7,972,325, 7,976,163, 7,988,292, and 8,126,246, which are incorporated by reference in their entirety.

In some embodiments, the Purkinje reflections measured pre operatively can be used to create a reference point to the center of the lens as well as determine the relative location of other important surfaces within the eye. One example would be ensuring that the wavefront measured preoperatively is transferred correctly with the right orientation and centration to the eye to allow for a more precise surgical treatment. The Purkinje reflections can be measured simultaneously with the wavefront measurement on an aberrometer or on iDesign and the wavefront scan center tied to the calculated geometric center of the lens calculated from the Purkinje reflections. The center of the wavefront can also be tied to the difference between the center point of the lens (using the Purkinje III and Purkinje IV reflections) to the center point of the Purkinje I reflection, which is from the anterior side of the cornea. This gives a relative reference point to the discrepancy in distance between the cornea center compared to the center of the lens. This can be used to align the wavefront measurement to optimize treatment as well. Additional references can be created using the Purkinje reflections (I, III, and/or IV) and tied to Optical Coherence Tomography (OCT) measurements, confocal microscopy measurements, or slit lamp images. All of this can help the surgeon for planning a surgical treatment and ensure that the measurements are correctly input and aligned, allow for a center capsulorhexis, and thus centered IOL placement allowing for optimal surgical outcomes.

Figure 8:
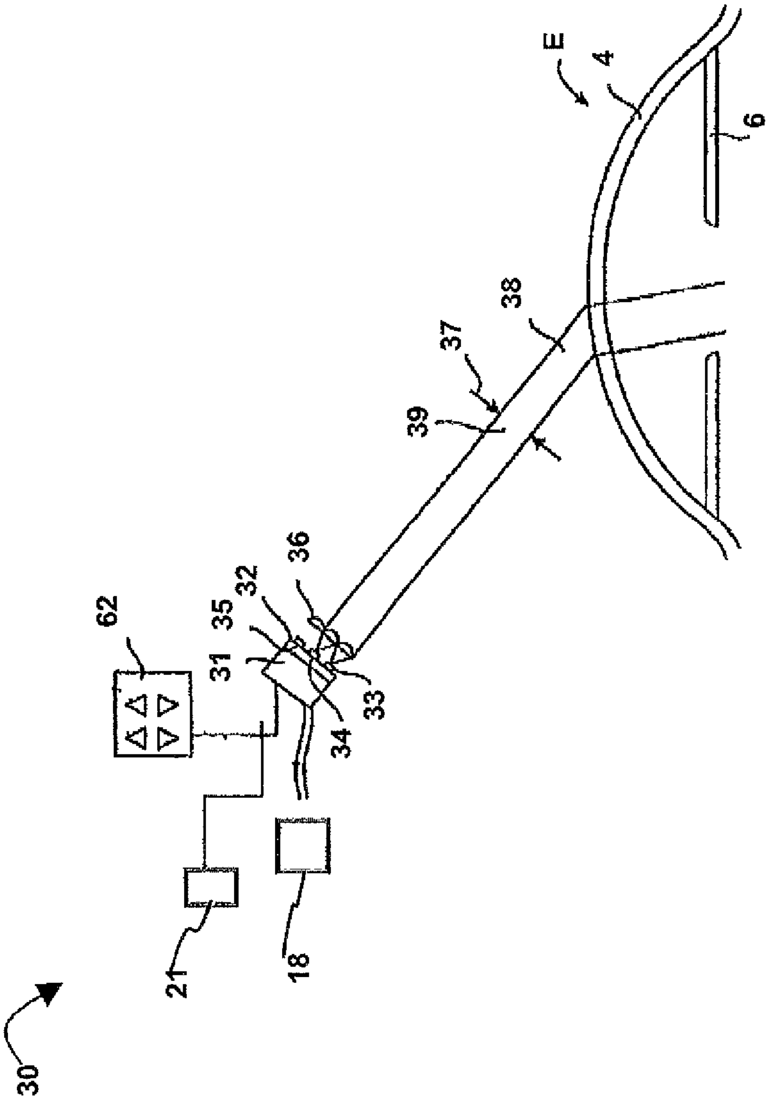
FIG. 8 illustrates an eye illuminated with a slit lamp according to an embodiment of this invention.

In some embodiments, the system 100 can be incorporated into a slit lamp fitted with an IR illumination source to allow for visualizing the whole capsular bag through the iris and correlating the center of the lens based off the Purkinje reflections to visual center. FIG. 8 illustrates, in an embodiment, an eye E having a cornea 4 and an iris 6 illuminated with a slit lamp 30 having a shaped beam of light 38 having a cross-section 39 with a size 37 across a cross-section 39. An LED array 32 is positioned near a micro-lens array 36. LED array 32 comprises a plurality of individual LEDs such as LEDs 33, 34 and 35. Micro-lens array 36 is positioned a focal length from the individual LEDs to collimate light emitted from the LEDs as the shaped light beam 38, which travels toward the eye E. In the example of FIG. 8, a portion of LED array 32 comprising LEDs 33 and 34 emits light. The size 37 across the cross-section 39 of the beam 38 is determined by a number of LEDs emitting light. An operator views the eye E through a microscope (not shown here, but for clarity, see incorporated U.S. Pat. No. 7,338,169 and other herein incorporated patents for further detail). An imaging device 18 may be mounted on the slit lamp 30 to image the eye E or the same imaging system can be used as system 100.

An LED driver (which may also be referred to herein as a computer system or system 206) 31 selectively drives any combination of LEDs 33, 34 and 35 of LED array 32. A user interface input device 62 is operationally coupled to the LED driver 31. The user interface input device 62 includes one more controls that adjust the size 37 across the cross-section 39 of the shaped light beam 38. The one or more controls of the user interface input device 62 also send one or more signals to the LED driver 31. The LED driver 31 selectively drives the LEDs of the LED array 32 in response to the one or more signals from the one or more controls. Another one or more controls of the user interface input 62 adjust an intensity of the light beam 38. An automated image analysis system 21 may be operatively coupled to the LED driver 31 to automatically adjust the light beam 38. For patient comfort, the visible part of the spectrum of the slit illumination can be filtered out using infrared (IR) glass filters, for example, filters RG715, RG830, RG850, or RG780 manufactured by SCHOTT North America, Inc, Elmsford, N.Y. One or more filters can be mounted in the filter turret (not shown) of the slit lamp illuminator. From this, the lens capsule will be visible and system 206 can be used to identify the outer edge of the bag. While the bag diameter, size and shape is recorded, the center can be determine using the Purkinje III and IV reflection and combined with the measurements taken from the slit lamp. This will serve as a reference measurement for the surgeon to go back to while preparing for surgery or during surgery independent of the pupil location. This will serve as a mechanism to compensate for a papillary decenter shift. Based on the center determined from the Purkinje reflections under the surgical microscope, the doctor will know the relative size of the bag and where to anticipate the edges to be. This can also aid in determining how large of a capsulorhexis to create to ensure that radial tears of the bag do not occur, thus reducing complications intra-operatively.

Alternatively, the system 100 may be incorporated into and implemented as part of a device or system that is used to generate ultra-short pulsed laser beams that have pulse durations in the femtosecond range, as described in U.S. Pat. Nos. 4,764,930 and 5,993,438. Certain ultra-short pulsed laser systems are used for ophthalmic surgeries across wavelength ranges from UV to NIR. For example, U.S. Pat. No. 5,993,438 discloses a laser device for performing ophthalmic surgical procedures to effect high-accuracy corrections of optical aberrations. Further details of suitable systems for performing laser ophthalmic can be found in commonly-assigned U.S. Pat. Nos. 4,665,913, 4,669,466, 4,732,148, 4,770,172, 4,773,414, 5,207,668, 5,108,388, 5,219,343, 5,646,791 and 5,163,934. The system 100 can be implemented into a surgical system to give real time feedback to the surgeon to ensure that the center of lens and/or the relative position of the apex of the cornea with respect to the center of the lens is always know.

Figure 9:
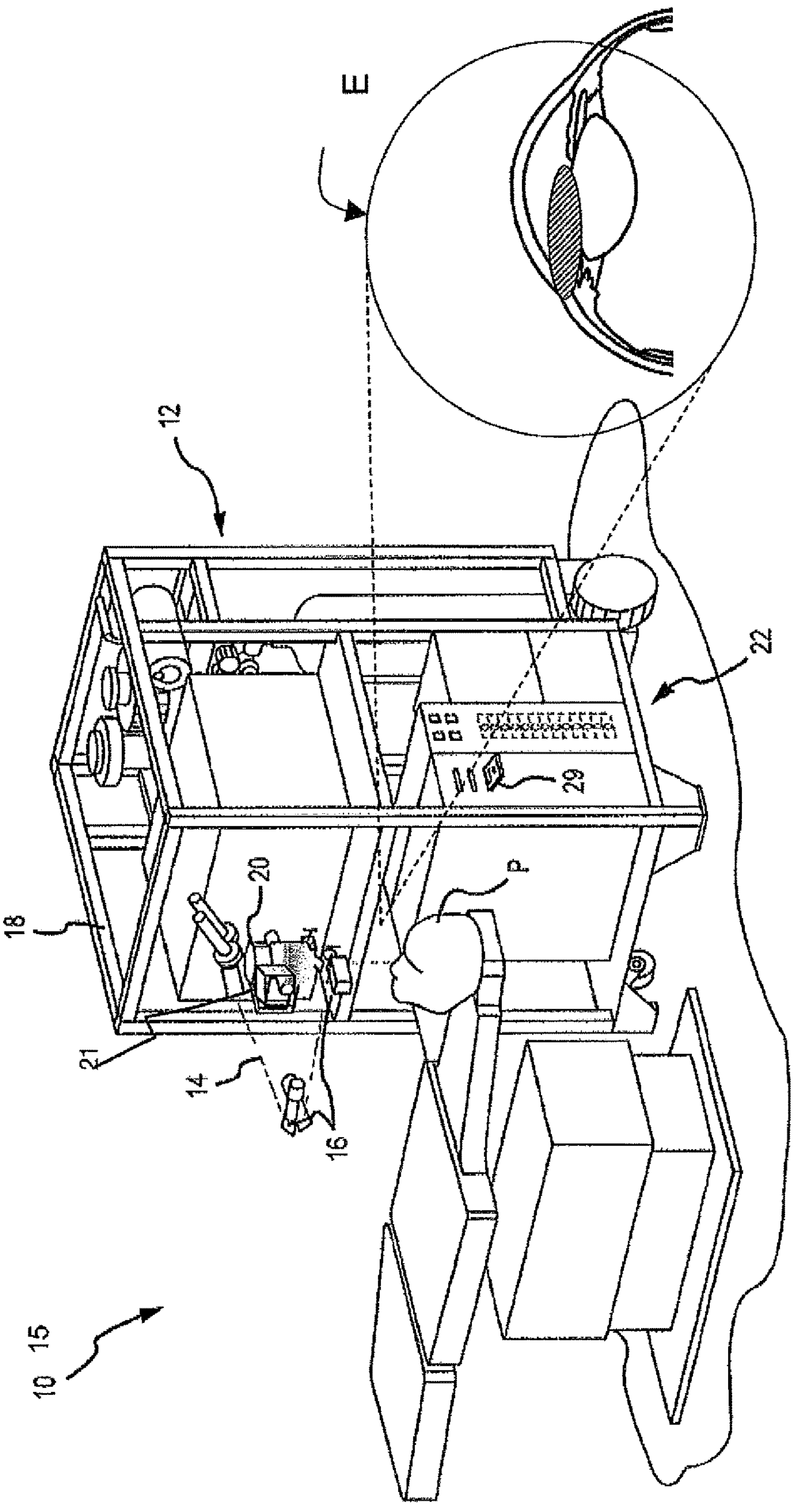
FIG. 9 illustrates a laser surgery system according to an embodiment of this invention.

FIG. 9 illustrates a laser surgery system 15. In an embodiment, the laser surgery system 15 includes a laser assembly 12 that produces a laser beam 14. Laser assembly 12 is optically coupled to laser delivery optics 16, which directs laser beam 14 to an eye E of a patient. An imaging assembly 20, including a microscope, is mounted on a delivery optics support structure (not shown here, but for clarity, see incorporated U.S. Pat. No. 7,931,371 and other herein incorporated patents for further detail) to image the cornea of eye E during the laser procedure. This will allow the surgeon to not only visually register the cornea both as a slit lamp image but also be able to locate the apex (center) of the cornea relative to the lens. This will further allow the surgeon to optimize his/her treatment plan to correlate these measurements to the given procedure he/she is performing. The slit lamp with IR illumination will also expose the capsular bag visually and the surgeon can register the geometric center of the lens based off the Purkinje images as well as monitor his capsulorhexis size with respect to the bag size during the procedure. This will ensure that the capsulorhexis is centered over the eye, the diameter isn't too large for the bag size, and give feedback inter-operatively to ensure that no procedural failures occur, such as radial tears. This will also give a registered center point of the lens to allow the surgeon to target for his phacoemulisfication treatment (to remove the lens). Knowing the location of the center will allow the surgeon to target the nucleus with higher energy, while minimizing the overall energy pumped into the eye.

In one embodiment, the system 100 is implemented to determine the center of the lens when the patient's eye is applanated by a contact lens in a patient interface device, such as Abbott Medical Optics' Intralase patient interface used in conjunction with the iFS™ Advanced Femtosecond Laser System or the Intralase™ FS Laser System. This patient interface can be a curved or flat cone with an interface of flat applanation or liquid interface or have no interface/cone at all. An exemplary patient interface device adapted to interface between the laser surgical system and the eye for purposes of aligning the eye with the laser system is generally described in commonly-assigned U.S. Pat. No. 7,611,507, issued to Raksi, et al., which is incorporated herein in its entirety. Other examples of ophthalmic patient interface devices used to stabilize the eye are described in U.S. Pat. No. 6,863,667, issued to Webb et al., U.S. Pat. No. D462,442 issued to Webb, U.S. Pat. No. 6,623,476, issued to Juhasz et al., and co-pending U.S. patent application Ser. No. 13/230,590, which are incorporated here by reference.

In another embodiment, the system 100 can be used as a post-operative check on IOL placement. Reflections measured off of the IOL surface in conjunction with the slit lamp IR image can be used to verify that the IOL is center within the capsulorhexis and stable in the bag. Relative placement of the IOL center with respect to the cornea center can be measured and compared post-operatively with the pre-operative measurements to determine differenced in before/after vision measurements. This will become increasingly important with accommodating IOLs.

The embodiments described herein thus provide techniques for accurate determination of the location of the center of an eye lens. Such techniques can be used for any ophthalmic procedure requiring accurate determinations. These techniques can thus be used to improve the effectiveness of a wide variety of different ophthalmic procedures.

This disclosure has been provided in an exemplary form with a certain degree of particularity, and describes the best mode contemplated of carrying out the invention to enable a person skilled in the art to make or use embodiments of the invention. Those skilled in the art will understand, however, that various modifications, alternative constructions, changes, and variations can be made in the system, method, and parts and steps thereof, without departing from the spirit or scope of the invention. Hence, the disclosure is not intended to be limited to the specific examples and designs that are described. Rather, it should be accorded the broadest scope consistent with the spirit, principles, and novel features disclosed as generally expressed by the following claims and their equivalents.

What is claimed is:

1. An eye imaging assembly comprising:

an illumination device positioned to illuminate a patient's eye, the illumination device configured to emit one or more light beams from the illumination device;

an imaging device comprising a detector positioned to capture one or more images of the patient's eye;

a processor operatively coupled to the illumination device and the imaging device; and a non-transitory computer readable medium that stores a computer program that, when executed, causes the processor to perform or enable the following steps:

emit the one or more light beams into the patient's eye;

detect one or more eye images with the detector of the imaging device, the one or more eye images comprising a single Purkinje III reflection which is a reflection of the one or more light beams by an anterior surface of a lens of the eye and which forms a part of a circle, and a single Purkinje IV reflection which is a reflection of the one or more light beams by a posterior surface of a lens of the eye and which forms a part of another circle;

determine a Purkinje III diameter and a Purkinje III center location which are respectively a diameter and a center of the circle of the single Purkinje III reflection;

determine a Purkinje IV diameter and a Purkinje IV center location which are respectively a diameter and a center of the circle of the single Purkinje IV reflection;

determine a distance between the Purkinje III center location and the Purkinje IV center location; and determine a location of a center of the lens of the eye using only the Purkinje III diameter, the Purkinje III center location, the Purkinje IV diameter, the Purkinje IV center location, and the distance between the Purkinje III center location and the Purkinje IV center location which have been determined from the single Purkinje III reflection and the single Purkinje IV reflection.

2. The eye imaging assembly of claim 1, wherein the location of the center of the lens of the eye is determined as corresponding to a position on a line between the Purkinje III center location and the Purkinje IV center location at a distance $X_1$ from the Purkinje III center location, where $X_1$ is defined as:

$$X_1 = L\left(\frac{D_4}{D_3 + D_4}\right),$$

where L is defined as the distance between the Purkinje III center location and the Purkinje IV center location, $D_3$ is defined as the Purkinje III diameter, and $D_4$ is defined as the Purkinje IV diameter.

3. The eye imaging assembly of claim 1, wherein the location of the center of the lens of the eye is determined as corresponding to a position on a line between the Purkinje III center location and the Purkinje IV center location at a distance $X_2$ from the Purkinje IV center location, where $X_2$ is defined as:

$$X_2 = L\left(\frac{D_3}{D_3 + D_4}\right),$$

where L is defined as the distance between the Purkinje III center location and the Purkinje IV center location, $D_3$ is defined as the Purkinje III diameter, and $D_4$ is defined as the Purkinje IV diameter.

4. The eye imaging assembly of claim 1, wherein the computer program, when executed, causes the processor to control the illumination device so as to adjust the one or more light beams until a position and/or a boundary of the lens capsule is detected.

5. The eye imaging assembly of claim 1, wherein the wavelength of the one or more light beams is infrared or near infrared.

6. The eye imaging assembly of claim 1, further comprising a guided user interface comprising a display, and wherein the calculated center is outputted onto the guided user interface (GUI) display.

7. The eye imaging assembly of claim 1, wherein the one or more eye images detected with the detector of the imaging device comprises a Purkinje I reflection, and wherein the computer program, when executed, causes the processor to determine the Purkinje I diameter and a Purkinje I center location.

8. The eye imaging assembly of claim 1, further comprising a wavefront aberrometer operatively coupled to the processor, the wavefront aberrometer being configured to measure a wavefront reflected from the eye of the patient.

9. The eye imaging assembly of claim 8, wherein the computer program, when executed, causes the processor to control the imaging device and the wavefront aberrometer so as to simultaneously measure the Purkinje III reflection, the Purkinje IV reflection and the wavefront reflected from the eye of the patient.

10. The eye imaging assembly of claim 9, wherein a center of the wavefront is correlated to the center of lens of the eye.

11. The eye imaging assembly of claim 8, wherein the one or more eye images detected with the detector of the imaging device comprises a Purkinje I reflection, wherein the computer program, when executed, causes the processor to determine the Purkinje I diameter and a Purkinje I center location, and wherein the Purkinje I reflection is measured simultaneously with the Purkinje III reflection, Purkinje IV reflection and the reflected wavefront.

12. The eye imaging assembly of claim 8, wherein the one or more eye images detected with the detector of the imaging device comprises a Purkinje I reflection, wherein the computer program, when executed, causes the processor to determine the Purkinje I diameter and a Purkinje I center location, and wherein a center of the reflected wavefront is correlated to a difference between the center point of the lens of the eye to the center point of the Purkinje I reflection.

* * * * *